United States Patent [19]

Zavadsky et al.

[11] Patent Number: 5,895,694
[45] Date of Patent: Apr. 20, 1999

[54] CHLORINE-FREE MULTILAYER FILM MATERIAL, PROCESS FOR ITS MANUFACTURE AND ITS USE

[75] Inventors: Emil Zavadsky, Ollon, Switzerland; Vittorio Perego, Busto Arsizio, Italy

[73] Assignee: W. R. Grace & Co.-Conn., Duncan, S.C.

[21] Appl. No.: 08/523,979

[22] Filed: Sep. 6, 1995

[30] Foreign Application Priority Data

Sep. 7, 1994 [EP] European Pat. Off. ............ 94114057

[51] Int. Cl.$^6$ .................................................. B32B 27/32
[52] U.S. Cl. .................... 428/36.7; 428/35.4; 428/475.8; 428/476.3; 428/483; 428/515; 383/108; 383/113; 604/332
[58] Field of Search .................................. 428/35.4, 36.7, 428/36.91, 336, 475.8, 476.3, 483, 515, 261, 349; 604/332; 383/108, 113

[56] References Cited

U.S. PATENT DOCUMENTS

| | | | |
|---|---|---|---|
| 4,239,826 | 12/1980 | Knott, II et al. | 428/35 |
| 4,254,169 | 3/1981 | Schroeder | 428/36.7 |
| 4,572,854 | 2/1986 | Dallmann et al. | 428/35 |
| 5,212,246 | 5/1993 | Ogale | 525/240 |
| 5,316,826 | 5/1994 | Kotani et al. | 428/172 |
| 5,399,396 | 3/1995 | Ohlsson et al. | 428/36.7 |
| 5,455,091 | 10/1995 | Oreglia et al. | 428/36.7 |

FOREIGN PATENT DOCUMENTS

| | | |
|---|---|---|
| 0118060B2 | 2/1984 | European Pat. Off. . |
| 0318025 | 11/1988 | European Pat. Off. . |
| 0588667A2 | 9/1992 | European Pat. Off. . |
| 0625343A2 | 8/1994 | European Pat. Off. . |
| 274386A1 | 12/1989 | Germany . |
| 274387A1 | 12/1989 | Germany . |
| 4100350A1 | 1/1991 | Germany . |
| 2212167 | 7/1989 | United Kingdom . |
| WO 93/11938 | 6/1993 | WIPO . |

OTHER PUBLICATIONS

Doak, Kenneth W., "Low Density Polyethylene", Encyclopedia of Polymer Science & Engineering, vol. 6, pp. 386 and 413, 1992.

*Primary Examiner*—Charles Nold
*Attorney, Agent, or Firm*—Thomas C. Lagaly

[57] ABSTRACT

The present invention relates to a chlorine-free multilayer film material comprising a) a gas-barrier layer (1) comprising a non-chlorine containing organic polymer which is substantially impermeable to oxygen gas;

b) two tie layers (2) each contacting one side of said barrier layer;

c) an inner surface layer (3);

d) an outer surface layer (4); and e) two intermediate layers (5) positioned between said surface layers (3,4) and said tie layers (2), said barrier layers (5) comprising an ethylene-propylene copolymer having a flexural modulus of less than 200 MPa and preferably less than 150 MPa. a process for the manufacture of this film material and its use for the manufacture of bags and pouches for ostomy/urostomy use.

19 Claims, 1 Drawing Sheet

CHLORINE-FREE MULTILAYER FILM MATERIAL, PROCESS FOR ITS MANUFACTURE AND ITS USE

BACKGROUND OF THE INVENTION

The present invention relates to a chlorine-free multilayer film material, a process for its manufacture and its use for the manufacture of bags and pouches for ostomy/urostomy use.

Multilayer film materials having gas- and odour-barrier properties are well known and widely used in medical and food packaging industries.

These films comprise a core barrier layer which may contain chlorine or be chlorine-free. The chlorine-containing barrier resin most commonly employed is polyvinylidene chloride (PVDC), i.e. a copolymer of vinylidene chloride monomers with one or more ethylenically unsaturated comonomers copolymerizable therewith, such as vinyl chloride, alkylacrylates, alkyl methacrylates, acrylonitrile, etc. The barrier properties of PVDC are extremely high and are not deteriorated by the presence of moisture which in some applications is always present. However, PVDC presents a number of environmental disadvantages, especially relating to incineration of these materials after use.

It is well known in fact that PVDC is hazardous to the environment and to personal health. Upon incineration hydrochloric acid and potentially also polychlorinated dibenzodioxin and furan toxins are formed, which represent substantial environmental problems.

Chlorine-free barrier layers include vinyl alcohol comprising polymers, such as typically ethylene-vinyl alcohol (EVOH) copolymers and poly(vinyl alcohol) (PVAL), and—with lower barrier properties—polyamides, polyesters, polystyrenes.

While the barrier properties of the vinyl alcohol comprising polymers are very high under dry conditions, they are rapidly deteriorated in the presence of moisture.

In highly demanding applications, such as in the case of pouches for drainage of human body liquids, where the film is necessarily in contact with moisture but at the same time it is extremely important that the barrier layer retains its properties for as long as possible, barrier structures comprising a PVDC layer are widely appreciated in spite of the disadvantages indicated above. In particular the applicant company is currently manufacturing a film comprising a layer of PVDC sandwiched between opposing layers of EVA for use in the manufacture of ostomy pouches. Besides possessing high barrier properties, this structure also has mechanical properties (softness, quietness, resistance) which render it particularly suitable for this application. Chlorine-free structures have been proposed also for these highly demanding applications but their performances are however far from those obtainable with PVDC-based structures.

Therefore, there exists a great need for a chlorine-free multilayer film structure for the manufacture of bags and pouches specifically for medical use, such as for the manufacture of ostomy/urostomy pouches, which combines the advantage of being chlorine-free with barrier properties to gases and odours as well as with overall mechanical properties as close as possible to those of PVDC-based structures.

DE-A-41 00 350 discloses a seven layer chlorine-free barrier packaging material for infusion solutions. The material comprises a base material consisting of a coextruded film made of an ethylene-vinyl alcohol copolymer and two coating polyethylene layers on both surfaces thereof, onto which a polyethylene layer and an ethyl-vinyl acetate copolymer layer are extrusion laminated.

EP-A-0 588 667 covers a multiple layer film useful in moisture barrier packaging applications, such as for the packaging of food products which require protection from the environment. One preferred embodiment of said thermoplastic multi-layer film materials comprises a core layer made of an oxygen barrier material, such as an ethylene-vinyl alcohol copolymer, two intermediate layers provided on said core layer comprising a propylene polymer or copolymer or a polymeric adhesive, such as a carboxylic acid or maleic anhydride-modified polyolefin such as polypropylene-based carboxylic acid or maleic anhydride-modified polyolefin, moisture barrier layers comprising a blend of a propylene polymer or copolymer and a hydrocarbon resin and outermost layers covering the outer surfaces comprising propylene polymer or copolymer.

International patent application WO 93/11 938 relates to multilayered barrier structures for use in the manufacture of ostomy pouches. Said multilayered barrier structure comprises a five-layer material consisting of a gas barrier layer, two moisture barrier layers and optionally one or more adhesive layers disposed therebetween. The moisture barrier layer comprises a mesophase propylene-based material which contacts at least one of the sides of the non-chlorine gas barrier layer preferably made of an ethylene-vinyl alcohol copolymer. Said mesophase propylene-based material is stated to unexpectedly enhance the overall properties of the multilayered barrier structure.

Multilayer films comprising a gas and aroma barrier layer are disclosed as well in EP-B-0 1 18 060. The seven-layer composite film material comprises an inner barrier layer based on a saponified ethylene-vinylacetate copolymer, layers immediately adjacent to each of the two surfaces of said barrier layer comprising an adhesion promoting material of a modified polyolefin or a partially saponified ethylene-vinyl acetate copolymer on which a first layer made out of polypropylene or an ethylene-propylene copolymer is attached, which carries sealable outer layers made of an olefin homo- or copolymer. All the layers of the multilayered, dimensionally stable, sealable film are biaxially oriented with identical stretching ratios and heat-set.

U.S. Pat. Nos. 4,239,826 and 4,254,169 disclose multilayer barrier films having a core gas barrier layer of a vinyl alcohol polymer or copolymer between opposing layers of a polyolefin blended with a chemically-modified polyolefin such as a vinyl acetate-vinyl alcohol copolymer, a vinyl alcohol-ethylene-vinyl acetate terpolymer or high density polyethylene with an unsaturated fused-ring carboxylic acid grafted thereto. The multi-layer barrier films of these documents are stated to be useful for the manufacture of containers in which foods are packaged.

DD-A-274 386 and DD-A-274 387 disclose coextruded composite films used for bags and pockets for human medicine, such as for ostomy bags, which comprise five layers and contain as the core gas barrier layer an ethylene-vinyl alcohol copolymer. Between the outer layers made of an ethylene-vinyl acetate copolymer and a blend of linear low density polyethylene and very low density polyethylene, respectively, and the core layer adhesive layers are inserted made of an ionomer resin.

5-layer chlorine-free ostomy pouches are already on the market. They share a core oxygen-barrier layer which comprises EVOH, two tie layers of modified ethylene-vinyl acetate copolymers on both sides of the core layer and two surface layers consisting of or comprising EVA.

While said multilayer films are free of chlorine and therefore satisfy the requirement of environmental safety, they are not fully satisfying as to their physical properties, specifically their oxygen permeability and moisture vapor transmission rate. As a matter of fact their oxygen permeability which is very low under dry conditions (0% relative humidity) increases remarkably at 100% relative humidity and becomes strikingly different from that of a PVDC-comprising structure of the same overall thickness.

Also the odour barrier properties of these structures seem to be very different from those of the PVDC-structures.

The problem to be solved by the present invention therefore is the provision of a chlorine-free multilayer film material having mechanical and odour barrier properties comparable with that of standard polyvinylidene chloride based multilayer film materials of the same thickness.

This problem is solved by the chlorine-free multilayer film material according to claim 1. The subclaims relate to preferred embodiments thereof, a process for the manufacture of said material and the use of this material for the manufacture of bags and pouches for ostomy/urostomy use.

The present invention therefore provides a chlorine-free filmmaterial comprising a) a gas-barrier layer comprising a non-chlorine containing organic polymer which is substantially impermeable to oxygen gas;

b) two tie layers each contacting one side of said barrier layer;

c) an inner surface layer;

d) an outer surface layer; and e) two intermediate layers positioned between said surface layers and said tie layers, comprising an ethylene-propylene copolymer having a flexural modulus (measured according to ASTM D-882) of less than 200 MPa, preferably less than 150 MPa.

A further subject matter of the present invention is a process for the manufacture of said chlorine-free multilayer film material comprising coextruding the materials for the gas-barrier layer, the two tie layers, the intermediate layers, the inner surface layer and the outer surface layer, cooling the coextruded film material, collapsing the cooled film material and optionally laminating a non-woven film to the multilayer film material obtained to the outer surface layer.

As used herein, the terms "polymer" or "polymer resin" generally include but are not limited to homopolymers, copolymers, such as, for instance, block, graft, random, and alternating copolymers, etc. as well as blends and modifications thereof.

The term "copolymer" is intended to denote polymers of two or more comonomers.

SUMMARY OF THE INVENTION

The term "polyolefin" as used herein generally refers to thermoplastic polymers obtained by polymerization or copolymerisation of relatively simple ($C_2$–$C_{12}$)olefins which may contain other comonomers wherein the olefin units are however present in higher amounts with respect to the other comonomers; including, but not limited to, homopolymers, copolymers, terpolymers, blends and modifications of such relatively simple polyolefins. Are specifically included therein homopolymers such as polyethylene and polypropylene, propylene copolymers, ethylene-α-olefin copolymers, ethylene-vinyl acetate copolymers, and ethylene-acrylate or ethylene-methacrylate copolymers.

DEFINITIONS

The term "polyethylene" as used herein refers to a family of resins obtained by polymerizing ethylene molecules. By varying the catalysts and the methods of polymerization, properties such as density, melt index, crystallinity, degree of branching and molecular weight distribution can be regulated over wide ranges. Low density polyethylenes (LDPE) are those ethylene homopolymers which have densities below about 0.925 g/cc. The term "polypropylene" refers to a thermoplastic resin obtained by homopolymerizing propylene units according to known processes.

The term "ethylene-α-olefin copolymer" designates a copolymer of ethylene with one or more ($C_4$–$C_{18}$)-α-olefin preferably selected from the group comprising the linear copolymers or terpolymers of ethylene with 1-butene, 4-methyl-1-pentene, 1-hexene, and 1-octene. In particular, as used herein, linear low density polyethylene (LLDPE) is used to identify an ethylene-α-olefin copolymer having a density usually in the range of from about 0.915 g/cc to about 0.925 g/cc; linear medium density polyethylene (LMDPE), as defined here, an ethylene-α-olefin copolymer having a density usually in the range of from about 0.926 to about 0.941 g/cc; while very low density polyethylene (VLDPE), as used herein, an ethylene-α-olefin copolymer having a density lower than 0.915 g/cc. The term "ethylene-α-olefin copolymers" as used herein, is not limited to conventional Ziegler-Natta linear polyethylenes but also includes the so called metallocene, single site, or constraint-geometry ethylene-α-olefin copolymers.

The term "ethylene-vinyl acetate copolymer" (EVA) as used herein refers to a copolymer formed from ethylene and vinyl acetate monomers wherein the ethylene derived units in the copolymer are present in major amounts, typically from about 60 to about 98% and the vinyl acetate derived units in the copolymer are present in minor amounts.

As used herein the terms "ethylene acrylic acid" and "ethylene-acrylate" or "ethylene-methacrylic acid" or "ethylene-methacrylate copolymer" refers to the product obtained by copolymerisation of ethylene with acrylate or methacrylate monomers of formula $CH_2=C(R)=CO=OX$ wherein R is hydrogen or methyl and X is hydrogen, ($C_1$–$C_4$)alkyl, or a metal cation preferably selected from $Na^+$, $Zn^{++}$, wherein the ethylene units are present in a higher amount than the acrylate or methacrylate units. The above copolymers in free acid or ionized forms are also referred to as "ionomers". Suitable ionomers include those sold under the trademark Surlyn by DuPont.

The term "ethylene-vinyl alcohol" or EVOH refers to a copolymer comprising from about 30 to 50% by weight of ethylene derived units.

The term "polyamide" means a high molecular weight polymer having amide images, and refers more specifically to synthetic polyamides, either aliphatic or aromatic, either in crystalline or amorphous form and to blends thereof. Exemplary of synthetic polyamides are various nylons.

The term "polystyrene" generally refers to those polymers which are obtainable by polymerization of styrene or styrene derivatives, e.g. divinylbenzene, vinyltoluene, and α-methylstyrene, or copolymerisation of the above monomers with other vinyl comonomers, e.g. butadiene, acrylonitrile, methyl acrylate, maleic anhydride, and the like comonomers, as well as to the rubber modified polystyrenes (impact-resistant polystyrenes) and to their blends.

The term "polyester", as used herein, typically refers to bi-oriented, heat-set, polyethylene terephthalate.

BRIEF DESCRIPTION OF THE DRAWINGS

In the following the invention is disclosed more in detail with reference to the enclosed drawing which shows in the only FIG. 1 a schematic cross section of a preferred embodiment of the seven layer chlorine-free multilayer film material of the present invention.

Figure 1:
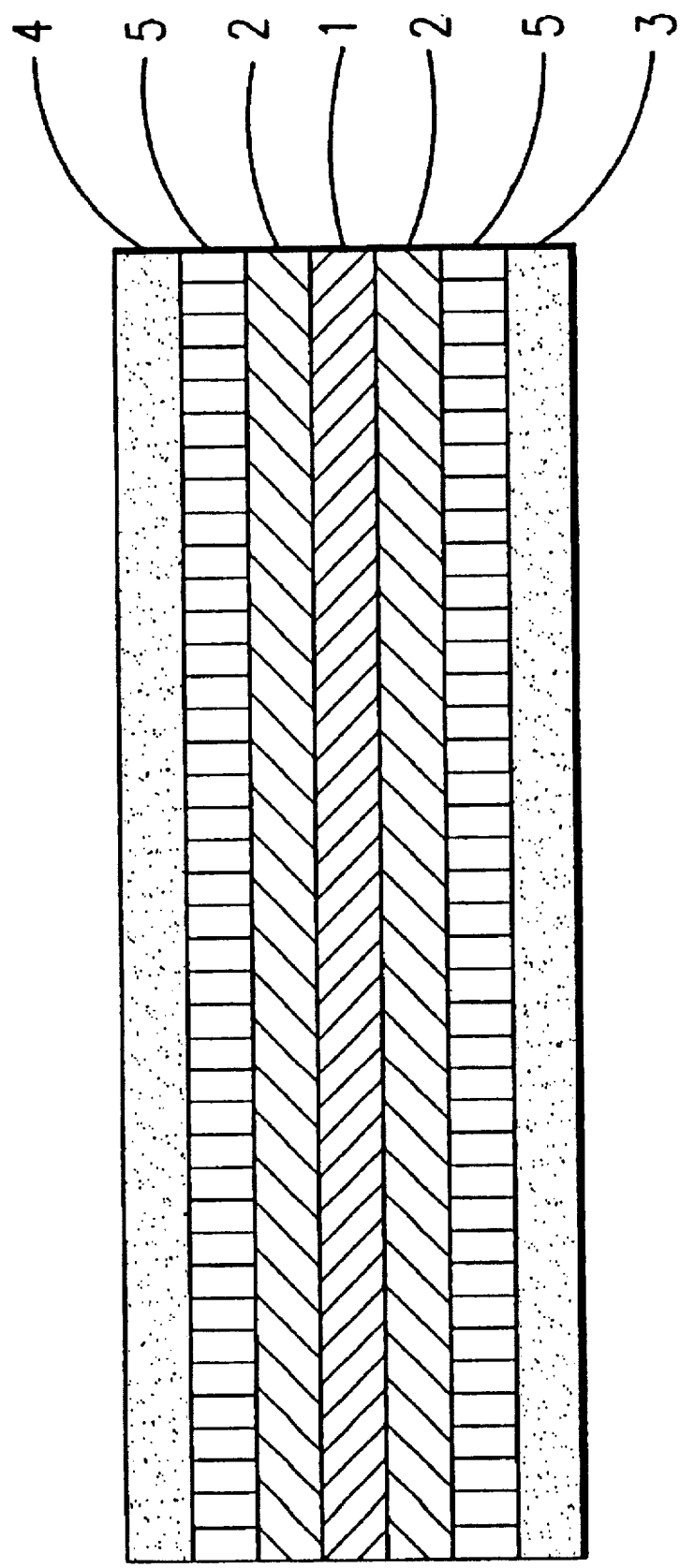
As shown in FIG. 1, the chlorine-free multilayer film material of the present invention comprises a gas-barrier layer 1 comprising a non-chlorine containing organic polymer which is substantially impermeable to oxygen gas. According to a preferred embodiment of the present invention said organic polymer of the gas-barrier layer 1 has an oxygen transmission rate of less than about 150, preferably less than about 100 and more preferably less than 70 $cm^3/m^2$·day·bar at 23° C. and 0% relative humidity. The organic polymer of said gas-barrier layer 1 may comprise an ethylenevinyl alcohol copolymer (EVOH), polyvinylalcohol (PVOH), a polyamide (PA), a polyester (PET) or a polystyrene (PS), which polymers may be used alone or in the form of mixtures of two or more of these products.

According to a preferred embodiment of the present invention the organic polymer for said gas-barrier layer 1 comprises ethylene-vinyl alcohol copolymer (EVOH). EVOH is generally obtained by a polymerization of ethylene with a vinyl ester followed by saponification. The degree of saponification is typically higher than 95% by mole and preferably is higher than 98% by mole. The EVOH may be a mixture of two or more EVOH having different ethylene content and/or different saponification degree. It may contain various additives such as antioxidants, colorants, ultraviolet absorbers, plasticisers, and the like agents, as well as various resins such as polyamides, polyolefins, etc. to the extent that they do not adversely affect the properties of the obtained film.

Preferred EVOH materials are, for example, EVAL® EP F 301B or EVAL® EP E105A (Kuraray) or Selar® OH 4416 (DuPont). Other EVOH materials of high (e.g. >44%) ethylene content are also preferred, thereby increasing the flexibility and softness of the structure at the thickness used.

The thickness of the gas-barrier layer 1 is not more than 20 μm and preferably in the range of about 3 to about 10 μm and more preferably in the range of about 5 to 8 μm, depending on the barrier properties of the resin employed.

Provided on both sides of said gas-barrier layer 1 and typically produced by coextrusion are tie layers 2, which each contact one side of said gas-barrier layer. Said tie layers 2 comprise modified polyolefins which carry anhydride or carboxylic acid groups as modifying units, modified ethylene-methyl acrylate copolymers, modified polypropylene and preferably modified ethylene-vinyl acetate copolymers (EVA).

The thickness of said tie layers 2 preferably is less than 10 μm and more preferably in the range of 2 to 8 μm and even more preferably in the range of 3 to 6 μm.

The multilayer film material of the present invention furtheron comprises on the side which is to become the inner side of an ostomy bag made therefrom an inner surface layer 3 which is a sealant layer and comprises a sealable polymer having either a dielectric dissipation factor sufficiently high to be sealable by radio frequencies (RF) or which is a heat-sealable polymer. Examples of polymers sealable by radio frequencies and useful for the manufacture of the inner surface layer 3 are ethylene-vinyl acetate copolymers alone or in the form of a blend with other polyolefins, such as polyethylene or linear polyethylene, preferably low density polyethylene (LDPE) or linear low density polyethylene (LLDPE). Said ethylene-vinyl acetate copolymer preferably comprises 10 to 28% and more preferably about 18% vinyl acetate units and optionally contains conventional slip and antiblocking agents, such as fatty amides (preferably primary or secondary amides) or ethylene-bis amides and natural or synthetic silica. As an alternative the inner surface layer 3 can be made from a heat-sealable polymer such as a very low density polyethylene (VLDPE), an ethylene-butyl acrylate copolymer (EBA), an ethylene-methacrylic acid copolymer (EMAA), an ionomer or a mixture thereof.

The outer surface layer or abuse layer 4 preferably is made from the same material as that used for the inner surface layer 3. It is, however, possible as well to manufacture the outer surface layer 4 which is coextruded with the other materials for the multilayer film material of the present invention from a material different from that of said inner surface layer 3 to provide specific properties on the outside of said abuse layer. In this case the polymer of said outer surface layer 4 can be selected from the group of polyolefins and from the polymers defined for use for the manufacture of the inner surface or sealant layer 3.

The thickness of the inner and the outer surface layers 3 and 4 is generally higher than 5 μm and preferably higher than 8 μm and more preferably in the range of 18 to 20 μm, each.

Key feature of the present invention is the provision of two intermediate layers 5 positioned between said surface layers 3 and 4 and said tie layers 2. These layers 5 comprise an ethylene-propylene copolymer having a flexural modulus of less than 200 MPa and preferably less than 150 MPa. Said flexural modulus being measured by ASTM Method D-882.

The ethylene-propylene copolymer to be used as the intermediate layers 5 is characterized by a high content of ethylene as the % of ethylene in said copolymer is higher than 10 and typically higher than 15. An additional comonomer, selected from the group of low molecular weight olefins, typically butene, may also be present.

Suitable examples of such polymers are products manufactured by Himont Company under the designations HIFAX® 7029 or Adflex 7029 or HIFAX® 7036 or Adflex 7036 or Adflex Q100F. The former product has a tensile modulus of 100 to 130 MPa (ASTM D-882), a tensile strength at yield of 7.5 to 8.5 MPa (ASTM D-882), a tensile strength at break of 33 to 39 MPa, an elongation at break of 850 to 1000% (ASTM D-882), an Elmendorff tear strength of 4.0 to 5.8 N, a dart testvalue (66 cm) of >1500 g and a haze of 60%. These properties have been determined on a blown film of a thickness of 50 μm.

The thickness of said layers 5 is generally from about 4 to about 25 μm, preferably about 6 to about 15 μm and more preferably about 9 to 12 μm.

The total thickness of the chlorine-free multilayer film material of the present invention is preferably from about 45 to about 120 μm and more preferably about 55 to 90 μm.

The oxygen permeability of the total film of the present invention preferably is below 50 and more preferably below 30 $cm^3/m^2$·d·bar at 23° C. and 0% relative humidity (as measured according to ASTM Method D-3985), while it will be <200 $cm^3/m^2$·d·bar and preferably <150 $cm^2/m^2$·d·bar at 23° C. and 100% relative humidity.

According to a further embodiment of the present invention the multilayer film material furtheron comprises a non-woven film laminated on the outer surface layer 4. In this case the thickness of the chlorine-free material according to the invention, before lamination, would be preferably from about 45 to about 70 μm and more preferably from about 45 to about 65 μm. This non-woven film may comprise a spun bonded polyester (PE), polypropylene (PP), very low density polyethylene (VLDPE), low density polyethylene (LDPE) and/or linear low density polyethylene (LLDPE) material having an area weight of from 15 to 50 g/m² and more preferably from about 20 to about 40 g/m². The non-woven film may be glue-laminated or, preferably, heat laminated to the multilayer film of the invention. Furthermore, the whole film or only part of it can be laminated depending on the type of end pouches which are desired. When the multilayer film according to the present invention is heat laminated to a non-woven layer, the layer which would be in contact with the non-woven film has to have a high affinity for the material of the non-woven film. When the non-woven film is a polyethylene, EVA is particularly preferred as the contact layer in the barrier film and will preferably comprise from 25 to 28% of vinyl acetate. The provision of such a non-woven film laminated to the outer surface layer provides more comfort for the person using an ostomy/urostomy bag made from this material.

The chlorine-free multilayer film material of the present invention can be produced by any method known in that art for the preparation of non-shrinkable, cast films and specifically by means of conventional techniques of melt-coextrusion of the suitably selected polymers using either circular or flat dies.

The different thermoplastic resins used for the gas-barrier layer 1, the two tie layers 2, the intermediate layers 5, the inner surface layer 3 and the outer surface layer 4, optionally additivated as necessary or suitable are fed continuously into their respective extruders, melted therein and then transported from a feed-block or combining adaptor into a die where the different polymers, one layer over and adhering to the other, exit the die slot.

The temperature of the extruders, the feed-block and the die will depend on the particular types of polymers used (their melting points on the one hand and their thermal stability on the other hand) and can be set up by the man skilled in the art.

When a circular die is employed, depending on the dimensions of the die lips and on the thickness required for the extruded multilayer film, this coextrusion step may be followed either by a rapid cooling step (using external air or a cascade of water) or by an expansion of the obtained molten tube by inflation with internal air pressure as the molten polymers of the multilayer film leave the die lip before they are cooled by external means.

In this latter process, commonly known as the "hot-blown"-process, the blow-up ratio (which is the ratio between the circumference of the blown film finally obtained and that of the die slit) is typically from 2 to 7 and preferably from 3 to 5.

In both cases the cooled film is then collapsed by nip rolls, optionally axially slit and unfolded to form a flat film and wound up either as a tube or a flat film.

When a flat die is employed, the flat sheet which exits the slot die is normally cooled on a temperature-controlled rotating roll or in a cooling liquid bath or by any other known cooling means and after an optional drying step is then wound up.

Instead of a simultaneous extrusion of all the different layers of the multilayer film material of the present invention, it is also possible to use the technique called "extrusion coating". More particularly, it would be possible to extrude one or coextrude more layers of the multilayer film material through the die to obtain the substrate structure and then extrusion coating this substrate structure with the hot molten polymers corresponding to the further layers of the overall structures as they exit the die.

However, a further subject matter of the present invention is a process for the manufacture of the chlorine-free multilayer film material which comprises melt-coextruding the thermoplastic resins for the gas-barrier layer 1, the two tie layers 2, the intermediate layers 5, the inner surface layer 3 and the outer surface layer 4, respectively, each resin optionally additivated as necessary, through a die, cooling the coextruded film material and optionally laminating a non-woven film to the multilayer film material obtained to the outer surface layer 4.

According to a preferred embodiment this process comprises using a circular die in the melt-coextrusion step, rapidly cooling the coextruded material or expanding the obtained molten tube by inflation with internal air pressure, cooling the film, collapsing it by nip rolls, optionally slitting it axially and unfolding it to form a flat film.

A further preferred embodiment of this process comprises using a flat die in the melt-coextrusion step, cooling the coextruded film material and optionally drying the film.

The multilayer film material according to the present invention offers a superior combination of properties, i. e. the advantage of being chlorine-free, a softness almost comparable with that of existing polyvinylidene chloride based ostomy films, an oxygen permeability at 100% relative humidity (measured according to ASTM D-3985 after four days of conditioning and keeping both material sides in contact with water) almost comparable with that of standard polyvinylidene chloride based ostomy/urostomy films and 40 to 50% lower in comparison to chlorine-free competitive materials and a water vapor transmission rate 30 to 40% lower in comparison to competitive materials.

Therefore, the films according to the present invention have high noiselessness and pliability characteristics and gas and odour barrier properties particularly at 100% relative humidity that render them particularly suitable for the manufacture of containers and bags intended for human drainage in medical applications. Therefore, a further subject matter of the present invention is the use of the chlorine-free multilayer film material of the present invention for the manufacture of bags and pouches for ostomy/urostomy use.

The invention is furtheron illustrated by the following Examples and Comparative Examples.

It is to be understood that, unless otherwise specifically indicated, all the percentages in this specification and in the appended claims are calculated on a by weight basis.

Example 1

A seven-ply chlorine-free film with a very low gas and odour permeability suitable for ostomy/urostomy applications is provided having the following structure:

A/B/C/D/C/B/A wherein

A: inner and outer layers (3,4) made of an ethylene-vinyl acetate copolymer with 18% vinyl acetate and a melt flow index (MFI) of 0.7 g/10 min, comprising about 0.1% of antiblock agents (silica) and about 0.4% of slip agents (fatty acid amides), having a thickness of 22 μm;

B: intermediate layers (5) made of an ethylene-propylene copolymer with a high content of ethylene, characterized by a flexural modulus of about 100 MPa (Hifax 7029 or Adflex 7029 or Adflex Q 100F manufactured by Himont) and having a thickness of 11 μm;

C: tie layers (2) made of a modified ethylene-vinyl acetate copolymer containing anhydride functionalities (Bynel CXA 3062 by DuPont) having a thickness of 3 μm;

D: Ethylene-vinyl alcohol copolymer with 44% of ethylene and MFI of 5.5 g/10' having a thickness of 7 μm.

The seven-ply structure is manufactured by flat cast coextrusion.

Example 2

A seven-ply film material having the same construction as that disclosed in Example 1 with the only difference that:

the thicknesses of the layers A, B, C, and D is 20, 5, 5, and 10 μm respectively.

Example 3

A seven-ply film material having the same construction as that disclosed in Example 2 with the only differences that the thicknesses of the layers A, B, C, and D is 22, 8, 5, and 5 μm respectively, and that the resin used in the tie layer C is a modified polypropylene (ADMER QB520E manufactured by Mitsui);

has been manufactured by the hot-blown method.

Example 4

A seven-ply film material having the same construction as that disclosed in Example 1 with the only differences that:

the thicknesses of the layers A, B, C, and D, is 14, 9, 4.5, and 8 μm respectively; and that the ethylene-vinyl acetate used in layers A comprises about 0.2% of antiblocking agents and 0.2% of slip agents;

is manufactured by flat cast coextrusion.

Example 5

A seven-ply film material having the same construction as that disclosed in Example 4 with the only difference that:

the thicknesses of the layers A, B, C, and D is 32.5, 9, 4.5, and 8 μm respectively;

is manufactured by flat cast coextrusion.

Example 6

A seven-ply chlorine-free film with a very low gas and odour permeability suitable for ostomy/urostomy applications is provided having the following structure:

A/B/C/D/C/B/E wherein

A: inner layer (3) made of an ethylene-vinyl acetate copolymer with 18% vinyl acetate and a MFI of 0.7 g/10 min. comprising about 0.3% of antiblock agents (silica) and about 0.4% of slip agents (fatty acid amides), having a thickness of 10 μm;

B: intermediate layers (5) made of an ethylene-propylene copolymer with a high content of ethylene, characterized by a flexural modulus of about 100 MPa (Hifax 7029 or Adflex 7029 or Adflex Q 100F manufactured by Himont) and having a thickness of 9 μm;

C: tie layers (2) made of a modified ethylene-vinyl acetate copolymer containing anhydride functionalities (Bynel CXA 3062 by DuPont) having a thickness of 4.5 μm;

D: Ethylene-vinyl alcohol copolymer with 44% of ethylene and MFI of 5.5 g/10 min having a thickness of 8 μm;

E: outer layer (4) made of an ethylene-vinyl acetate copolymer with 25% vinyl acetate and a MFI of 2 g/10 min comprising about 0.5% of antiblocking agent and about 0.7% of slip agents, having a thickness of 10μm.

The film is manufactured by flat cast coextrusion.

Example 7

The film of Example 6 is heat laminated to a non-woven layer of spun bonded linear polyethylene of 35 g/m².

The heat lamination has been carried out substantially as described in EP patent application 90 313 550.7.

Example 8

A seven-ply film material having the same construction as that disclosed in Example 1 with the only differences that:

the thicknesses of the layers A, B, C and D is 21, 5, 5, and 10 μm respectively; and that the ethylene-vinyl alcohol copolymer used in layer D has 44% of ethylene and a MFI of 16 g/10 min;

is manufactured by the hot-blown method.

Comparative Example 1

A three-layer material comprising a 21 μm thick PVDC layer coated on both sides with EVA (15% vinyl acetate) copolymer layers, each one 27 μm thick, was manufactured by the hot-blown method. This material is actually marketed for ostomy/urostomy applications.

Comparative Example 2

An ostomy film with a chlorine-free barrier layer actually on the market was collected and analyzed showing the following structure:

A/B/C/B/A wherein

A: inner and outer layers of EVA having an average thickness of 29 μm;

B: tie layers of modified EVA having an average thickness of 4 μm;

C: modified EVOH barrier layer having an average thickness of 5 μm;

Comparative Example 3

Another ostomy film with a chlorine-free barrier layer also on the market was collected and analyzed showing the following structure:

A/B/C/B/A wherein

A: inner and outer layers of EVA having an average thickness of 32 μm;

B: tie layers of modified EVA having an average thickness of 4 μm;

C: EVOH comprising barrier layer having an average thickness of 4 μm.

Oxygen permeability in different conditions, and moisture vapor transmission rate (MVTR) of the structures of the above examples and comparative examples have been evaluated and the results obtained are summarized in following Table 1.

Oxygen permeability is evaluated by measuring the oxygen transmission rate by ASTM method D-3985. The evaluation is carried out at 23° C. and under dry conditions (0% relative humidity) and under wet conditions (100% relative humidity (R.H.)). In this latter case the test is carried out after 4 day conditioning at 100% R.H. obtained by contacting both sides of the film with water.

Moisture vapor transmission rate (MVTR) is evaluated according to ASTM method F-1249 at 38° C. and 98% R.H.

TABLE 1

| Structure of | Overall thickness (μm) | Oxygen permeability (ml/d.m².bar) | | MVTR (g/d.m²) |
|---|---|---|---|---|
| | | 0% R.H. | 100% R.H. | |
| Example No. | | | | |
| 1 | 72 | 6.7 | 135 | 24 |
| 2 | 70 | 34 | 191 | 29 |
| 3 | 75 | 37 | 155 | 15 |
| 4 | 63 | 5.1 | 113 | 22.1 |
| 5 | 100 | 3.7 | 80 | 16 |
| 6 | 55 | 6.2 | 131 | 25.5 |
| 7 | — | 6.9 | — | 31 |
| Comp. Example | | | | |
| 1 | 75 | 50 | <50 | 10 |
| 2 | 73 | 3.5 | 264 | 34.2 |
| 3 | 75 | 4.8 | 316 | 41 |

The odor barrier properties of the chlorine free multilayer structures of the present invention have been more specifically evaluated by submitting representative films of the Examples and the Comparative Examples to organoleptic evaluations.

More particularly, 10×10 cm pouches are prepared with the selected films and filled with either 10 ml of a 2.5% aqueous solution of ammonia or with chopped onions (20 g). These pouches are then heat-sealed and kept at a temperature of 37° C. and 100% R.H. At given times samples of the filled pouches are smelled by a panel of trained judges and assigned a different score from 0 (no odor) to 4 (strong odor). The results obtained in these tests are reported in following TABLES 2 and 3 wherein the figures represent the average of the panelists' scores.

TABLE 2

| Simulant: Onions | | | | | | |
|---|---|---|---|---|---|---|
| | time (hours) | | | | | |
| Structure of | 0.5 | 1 | 2 | 3 | 5 | 7 |
| Example No. | | | | | | |
| 1 | 1.5 | 1.5 | 3.0 | 3.0 | 3.0 | 3.5 |
| 2 | 0.0 | 1.5 | 2.5 | 3.0 | 3.0 | 3.5 |
| Comparative Example No. | | | | | | |
| 2 | 2.0 | 2.5 | 3.5 | 4.0 | | |

TABLE 3

| Simulant: Ammonia | | | | | | |
|---|---|---|---|---|---|---|
| | time (hours) | | | | | |
| Structure of | 0.5 | 1 | 2 | 3 | 5 | 7 |
| Example No. | | | | | | |
| 1 | 2.0 | 3.5 | 4.0 | | | |
| 2 | 2.0 | 3.0 | 4.0 | | | |

TABLE 3-continued

| Comparative Example No. | | | |
|---|---|---|---|
| 2 | 3.0 | 3.5 | 4.0 |

What is claimed is:

1. A chlorine-free multilayer material comprising:
   a) a gas-barrier layer comprising a non-chlorine containing organic polymer which is substantially impermeable to oxygen gas;
   b) two tie layers each contacting one side of said barrier layer;
   c) an inner surface layer;
   d) an outer surface layer; and
   e) two intermediate layers separately positioned between said surface layers and said tie layers, said intermediate layers comprising an ethylene-propylene copolymer having a flexural modulus of less than 200 Mpa and an ethylene content of greater than 10 percent by weight, wherein, at least one of said inner surface layer and said outer surface layer is a sealant layer comprising a material which is sealable by radio frequencies.

2. The chlorine-free multilayer film material according to claim 1, wherein the organic polymer of said gas-barrier layer has an oxygen transmission rate of less than about 150 $cm^3/m^2$daybar at 23° C. and 0% relative humidity.

3. The chlorine-free multilayer film material according to claim 2, wherein the organic polymer of said gas-barrier layer comprises a material selected from the group consisting of ethylene-vinyl alcohol copolymer, polyvinyl alcohol, polyamide, polyester, polystyrene and mixtures of the foregoing materials.

4. The chlorine-free multilayer film material according to claim 3, wherein the organic polymer of said gas-barrier layer comprises an ethylene-vinyl alcohol copolymer.

5. The chlorine-free multilayer film material according to claim 1, wherein said tie layers comprise a material selected from the group consisting of modified polyolefins which carry anhydride or carboxylic acid groups as modifying units, modified ethylene-vinyl acetate copolymer, modified ethylene-methyl acrylate copolymers and modified polypropylene.

6. The chlorine-free multilayer film material according to claim 1, wherein said inner surface layer is a sealant layer comprising a material selected from the group consisting of polymers which are sealable by radio frequencies and heat-sealable polymers.

7. The chlorine-free multilayer film material according to claim 6, wherein said inner surface layer comprises as a polymer sealable by radio frequencies an ethylene-vinyl acetate copolymer alone or in the form of a blend with other polyolefins.

8. The chlorine-free multilayer film material according to claim 7, wherein said ethylene-vinyl acetate copolymer comprises 10 to 25% vinyl acetate units.

9. The chlorine-free multilayer film material according to claim 6, wherein said inner surface layer comprises as a heat-sealable polymer a material selected from the group consisting of very low density polyethylene, ethylene-butyl acrylate copolymer, ethylene-methacrylic acid copolymer, ionomer, and mixtures thereof.

10. The chlorine-free multilayer film material according to claim 1, wherein said outer surface layer is a sealant layer comprising a material selected from the group consisting of polymers which are sealable by radio frequencies and heat-sealable polymers.

11. The chlorine-free multilayer film material according to claim 6, wherein said outer surface layer comprises as a polymer sealable by radio frequencies an ethylene-vinyl acetate copolymer alone or in the form of a blend with other polyolefins.

12. The chlorine-free multilayer film material according to claim 6, wherein said outer surface layer comprises as a heat-sealable polymer a material selected from the group consisting of very low density polyethylene, ethylene-butyl acrylate copolymer, ethylene-methacrylic acid copolymer, ionomer, and mixtures thereof.

13. The chlorine-free multilayer film material according to claim 1, wherein said intermediate layers comprise an ethylene-propylene copolymer which optionally contains an additional monomer selected from low molecular weight olefins.

14. The chlorine-free multilayer film material according to claim 1, wherein the thickness of the gas-barrier layer is not more than 20 µm.

15. The chlorine-free multilayer film material according to claim 1 wherein the thickness of the tie layers is less than 10 µm.

16. The chlorine-free multilayer film material according to claim 1, wherein the thickness of the inner and the outer surface layers is higher than 5 µm.

17. The chlorine-free multilayer film material according to claim 1, wherein the thickness of the intermediate layers is from about 4 to about 25 µm.

18. The chlorine-free multilayer film material according to claim 1, wherein the total thickness of the chlorine-free multilayer film material is from about 45 to about 120 µm.

19. The chlorine-free multilayer film material according to claim 1, wherein the oxygen permeability of the total multilayer film material is below 50 $cm^3/m^2 daybar$ at 23° C. and 0% relative humidity (measured according to ASTM D-3985).

* * * * *